US006803576B2

United States Patent
Pretto et al.

(10) Patent No.: US 6,803,576 B2
(45) Date of Patent: Oct. 12, 2004

(54) ANALYTICAL METHOD TO MEASURE NITROGEN CONCENTRATION IN SINGLE CRYSTAL SILICON

(75) Inventors: Maria Giovanna Pretto, Merano (IT); Maria Porrini, Merano (IT); Roberto Scala, Merano (IT); Vladimir Voronkov, Merano (IT); Paolo Collareta, Merano (IT); Robert J. Falster, London (GB)

(73) Assignee: MEMC Electronic Materials, SPA, Novara (IT)

( * ) Notice: Subject to any disclaimer, the term of this patent is extended or adjusted under 35 U.S.C. 154(b) by 200 days.

(21) Appl. No.: 10/252,479

(22) Filed: Sep. 23, 2002

(65) Prior Publication Data

US 2003/0068826 A1 Apr. 10, 2003

Related U.S. Application Data

(60) Provisional application No. 60/323,827, filed on Sep. 21, 2001.

(51) Int. Cl.[7] .............................................. G01N 21/17
(52) U.S. Cl. .............................. 250/339.08; 250/339.01
(58) Field of Search ....................... 250/339.01, 339.06, 250/339.07, 339.08, 339.09, 340, 341.4, 341.6

(56) References Cited

U.S. PATENT DOCUMENTS 5,066,599 A * 11/1991 Kaneta et al. ................. 438/7

OTHER PUBLICATIONS

Yatsurugi, Y., et al., Concentration, Solubility, and Equilibrium Distribution Coefficient of Nitrogen and Oxygen in Semiconductor Silicon, J. Electrochem. Soc. 120, 1973, p. 975–979.

Watanabe, M., et al., Oxygen–Free Silicon Single Crystal Grown from Silicon Nitride Crucible, Semiconductor Silicon, 1981, p. 126–137.

Itoh, Y., et al., Calibration curve for infrared spectrophotometry of nitrogen in silicon, Appl. Phys. Lett. 47, Sep. 1, 1985, p. 488–489.

Abe, T., et al., Deep Level Generation–Annihilation in Nitrogen Doped FZ Crystals, Materials Research Society Symposium Proceedings, Dec. 2–5, 1985, vol. 59, p. 537–544.

Stein, Herman J., Nitrogen in Crystalline S1, Materials Research Society Symposium Proceedings, 1986, vol. 59, p. 523–535.

Suezawa, M., et al., Nitrogen–Oxygen Complexes as Shallow Donors in Silicon Crystals, Japanese Journal of Applied Physics, vol. 25, 1986, p. 859–861.

Suezawa, M., et al., The Nature of Nitrogen–Oxygen Complexes in Silicon, Japanese Journal of Applied Physics, vol. 27, No. 1, Jan. 1988, p. 62–67.

Wagner, P., et al., Nitrogen–Oxygen Complexes in Czochralski–Silicon, Appl. Phys. A 46, Mar. 14, 1988, p. 73–76.

QI, M. W., et al., The evidence for interaction of the N–N pair with oxygen in Czochralski silicon, Journal of Applied Physics, vol. 69, No. 6, Mar. 15, 1991, p. 3775–3777.

A. Hara, et al., Model for NL 10 thermal donors formed in annealed oxygen–rich silicon crystals, J. Appl. Phys., 75, Mar. 15, 1994, p. 2929–2934.

(List continued on next page.)

*Primary Examiner*—Constantine Hannaher
*Assistant Examiner*—Timothy Moran
(74) *Attorney, Agent, or Firm*—Senniger Powers (57) ABSTRACT

The present invention is a method for quantitatively measuring nitrogen in Czochralski silicon based on the detection of one or more N—O complexes by means of low temperature Fourier Transform infrared spectroscopy (LT-FTIR) in the far infrared spectral range (FIR).

58 Claims, 8 Drawing Sheets

Nitrogen concentration vs. sum of peaks areas
240 cm-1 & 249 cm-1

OTHER PUBLICATIONS

Rasmussen, F. Berg, et al., Identification of the Dominant Nitrogen Defect in Silicon, Physical Review Letters, vol. 72, No. 12, Mar. 21, 1994, p. 1882–1885.

Jones, R., et al., Theoretical and isotopic infrared absorption investigations of nitrogen–oxygen defects in silicon, Semicond. Sci. Technol., 9, 1994, p. 2145–2148.

Yang, D., et al., Nitrogen effects on thermal donor and shallow thermal donor in silicon, Journal of Applied Physics, vol. 77, No. 2, Jan. 15, 1995, p. 943–944.

Rasmussen, F. Berg, et al., The Nitrogen–pair oxygen defect in silicon, Materials Science and Engineering B36, 1996, p. 91–95.

Yang, D., et al., Effect of nitrogen–oxygen complex on electrical properties of Czochralski silicon, Applied Physics Letters, vol. 68, No. 4, Jan. 22, 1996, p. 487–489.

Shi, X. H., et al., Annealing Behavior of N–O Complexes in Si Grown Under Nitrogen Atmosphere, Solid State Communications, vol. 106, No. 10, 1998, p. 669–671.

Adachi, N., et al., Reduction of Grown–In Defects by High Temperature Annealing, Journal of the Electrochemical Society, vol. 147, Jan. 2000, p. 350–353.

Hockett, R. S., et al., The Measurement of Nitrogen in Silicon Substrates by Sims, Electrochemical Society Proceeding, vol. 2000–17, 2000, p. 584–595.

Yang, D., et al., Infrared absorption of nitrogen–oxygen complex in silicon, Materials Science and Engineering B72, 2000, p. 121–123.

Voronkov, V. V., et al., Shallow thermal donors in nitrogen-doped silicon, Journal of Applied Physics, vol. 89, No. 8, Apr. 15, 2001, p. 4289–4293.

* cited by examiner

Peak area with and without illumination 240 cm-1
[ 2 ppma Nitrogen] N-Type

FIG. 3B

Peak area with and without illumination 249 cm-1
[2 ppma Nitrogen] N-type

Nitrogen concentration vs. peak area
249 cm-1

FIG. 4B

Nitrogen concentration vs. peak area
240 cm-1

FIG. 4C

Nitrogen concentration vs. sum of peaks areas
240 cm-1 & 249 cm-1

FIG. 6

ANALYTICAL METHOD TO MEASURE NITROGEN CONCENTRATION IN SINGLE CRYSTAL SILICON

CROSS-REFERENCE TO RELATED APPLICATIONS

This application claims the benefit of U.S. Provisional Application No. 60/323,827, filed Sep. 21, 2001.

FIELD OF THE INVENTION

This invention relates to a method for determining the nitrogen concentration in single crystal silicon, and more particularly, to a method of using low temperature Fourier Transform infrared spectroscopy (LT-FTIR) in the far infrared spectral range (FIR) to determine the concentration of nitrogen in single crystal silicon produced in accordance with the Czochralski method.

BACKGROUND OF THE INVENTION

The properties of nitrogen in silicon have become a matter of interest in recent years for several reasons. For example, nitrogen is known to lock, or pin, crystal dislocations, it is know to impart strength and warp resistance to silicon with low oxygen concentrations, and it is known to form shallow thermal donors (STDs) with an ionization energy of 35–37 meV in as-grown and annealed silicon. In view of the important role nitrogen plays in silicon, several measurement techniques have been applied to study nitrogen in silicon, including infrared spectroscopy, luminescence, electron paramagnetic resonance, Hall effect, deep level transient spectroscopy, secondary ion mass spectroscopy (SIMS), and nuclear reaction analysis.

In addition to studying the effects of nitrogen in silicon, some of the foregoing methods have been used to determine the quantity of nitrogen in silicon. For example, SIMS has been used to determine the concentration of nitrogen in silicon. See R. S. Hockett and D. B. Sams, Electrochemical Society Proceeding, Volume 2000-17, p. 584. The detection limit for nitrogen in silicon using SIMS is about $1-2 \times 10^{14}$ atoms/cm$^3$, and is limited primarily by background nitrogen (i.e., the residual nitrogen in the chamber atmosphere after evacuation).

Fourier Transform infrared spectroscopy (FTIR) has also been used to determine the concentration of nitrogen in silicon. The presence of nitrogen in silicon gives rise to several IR absorption peaks. The peaks of interest for these FTIR nitrogen measurement methods occur within the medium infrared region (MIR) between about 600 and about 1000 cm$^{-1}$. Specifically, the two main nitrogen-related MIR absorption peaks are at about 963 and about 766 cm$^{-1}$ and are associated with the vibrational modes of the molecular nitrogen species (N—N). The most widely accepted of determining nitrogen concentration by FTIR uses the absorption peak at 963 cm$^{-1}$ for which a calibration coefficient of $1.83 \times 10^{17}$ cm$^{-2}$ has been determined. See Y. Itoh and T. Nozaki, Appl. Phys. Lett. 47, p. 488 (1985). The nitrogen concentration is determined by the equation:

$$[N](\text{atoms}/cm^3) = 1.83 \times 10^{17} \times \alpha(963 \ cm^{-1}). \quad (1)$$

The absorption peak at 766 cm$^{-1}$ has also been used and the calibration coefficient of is $4.45 \times 1016$ cm$^{-2}$. See P Wagner et al., Apply Phys. A 46, p. 73 (1988); and Watanabe et al., Semiconductor Silicon, p. 126 (1981). The nitrogen concentration is determined by the equation:

$$[N](\text{atoms}/cm^3) = 4.45 \times 10^{14} \times \alpha(766 \ cm^{-1}). \quad (2)$$

The intensity of the nitrogen-related absorption bands, or peaks, in the MIR is always low for a silicon comprising about $10^{15}-10^{16}$ atoms/cm$^3$ (the maximum absorbance is 0.1), and much lower than oxygen and carbon peaks in the MIR. Thus, the accuracy of determining nitrogen according to these methods is less than desirable especially at low nitrogen concentrations. Additionally, these methods are even less accurate for determining the nitrogen concentration in CZ silicon than in FZ silicon. This is because the calibration coefficient for 963 cm$^{-1}$ absorption peak was determined using float zone-grown (FZ) single crystal silicon in which the vast majority of the nitrogen is in molecular form with the small remaining fraction being primarily atomic. In contrast, in CZ silicon, a significant fraction of the nitrogen is in the form of N—O complexes, and as a result, using the foregoing method underestimates the total nitrogen concentration in CZ silicon.

Thus, a need continues to exist for a method of quickly and accurately determining the concentration of nitrogen in CZ silicon, especially at low concentration levels such as below about $1 \times 10^{14}$ atoms/cm$^3$.

SUMMARY OF THE INVENTION

Among the features of the invention, therefore, is the provision of a method for quantitatively measuring nitrogen in Czochralski silicon based on the detection of one or more N—O complexes by means of low temperature Fourier Transform infrared spectroscopy (LT-FTIR) in the far infrared spectral range (FIR); the provision of a method for quickly and accurately determining the concentration of nitrogen in single crystal silicon; and the provision of a method for detecting nitrogen at concentrations below about $1 \times 10^{14}$ atoms/cm$^3$.

Briefly, therefore, the present invention is directed to a method for measuring a concentration of nitrogen in a silicon sample by Fourier Transform infrared spectroscopy, the method comprising: annealing the silicon sample at an annealing temperature $T_a$ for an annealing time $t_a$ to saturate the silicon sample with nitrogen-oxygen complexes; performing Fourier Transform infrared spectroscopy to measure an absorbance value related to the concentration of nitrogen-oxygen complexes in the annealed silicon sample; and calibrating the absorbance value to a nitrogen concentration value.

The present invention is also directed to a method for measuring a concentration of nitrogen in a silicon sample by Fourier Transform infrared spectroscopy, the method comprising: annealing the silicon sample at an annealing temperature $T_a$ for an annealing time $t_a$ to saturate the silicon sample with nitrogen-oxygen complexes, wherein $T_a$ is selected as a function of a detection limit for the nitrogen-oxygen complexes; performing Fourier Transform infrared spectroscopy to measure an absorbance value related to the concentration of nitrogen-oxygen complexes in the annealed silicon sample; and calibrating the absorbance value to a nitrogen concentration value.

Additionally, the present invention is directed to a method for detecting a measurement of concentration of nitrogen in a silicon sample by Fourier Transform infrared spectroscopy, the method comprising: annealing the silicon sample at an annealing temperature $T_a$ for an annealing time $t_a$ to saturate the silicon sample with nitrogen-oxygen complexes, wherein $T_a$ is selected as a function of annealing time available to saturate the silicon sample with nitrogen-oxygen complexes; performing Fourier Transform infrared spectroscopy to measure an absorbance value related to the concentration of nitrogen-oxygen complexes in the annealed silicon sample; and calibrating the absorbance value to a nitrogen concentration value.

In another embodiment, the present invention is directed to a method for detecting a measurement of concentration of nitrogen in a silicon sample by Fourier Transform infrared spectroscopy, the method comprising: annealing the silicon sample at an annealing temperature $T_a$ for an annealing time $t_a$ to saturate the silicon sample with nitrogen-oxygen complexes, wherein $t_a$ is selected as a function of a detection limit for the nitrogen-oxygen complexes; performing Fourier Transform infrared spectroscopy to measure an absorbance value related to the concentration of nitrogen-oxygen complexes in the annealed silicon sample; and calibrating the absorbance value to a nitrogen concentration value.

Other objects will be in part apparent and in part pointed out hereinafter.

DETAILED DESCRIPTION

The present invention is a method for quantitatively measuring nitrogen in Czochralski silicon based on the detection of one or more N—O complexes by means of low temperature Fourier Transform infrared spectroscopy (LT-FTIR) in the far infrared spectral range (FIR). The portion of the FIR of interest is between about 200 and about 300 cm$^{-1}$ wherein, in oxygen-containing silicon, nitrogen gives rise to a multiplicity of absorption peaks related to the electronic transition of nitrogen-oxygen complexes (N—O complexes or N—O).

Advantageously, the present invention provides increased sensitivity to nitrogen which allows detection of nitrogen at a concentration that is at least a one order of magnitude improvement below previously known methods. Specifically, the method of the present invention can be used to detect nitrogen at a concentration as low as about 5×10$^{12}$ atoms/cm$^3$. More specifically, depending on the resistivity of silicon and the type of dopant(s) in the silicon, the detection limit of the present invention can range from about 5×10$^{12}$ atoms/cm$^3$ to about 1×10$^{13}$ atoms/cm$^3$.

To determine the nitrogen concentration in a silicon ingot, at least one sample is sliced from the ingot and polished to a spectral or mirror finish in accordance with methods standard in the art. The thickness of the sample is preferably between about 2 mm and about 10 mm and more preferably about 5 mm. Most preferably the thickness of the sample will be optimized based on the ingot being tested. Specifically, the optimum thickness depends upon the concentration of dopant(s) in the ingot and is determined through routine testing. In general, as the concentration of dopant increases, the optimum thickness tends to decrease.

After being polished, the method of the present invention comprises determining the concentration of interstitial oxygen, $O_i$, in the sample. Preferably, this accomplished using the method for measuring the interstitial oxygen content of silicon by Fourier transform infrared (FTIR) spectroscopy as described in the American Society for Testing and Materials (ASTM) Designation F 1188-93 entitled "Standard Test Method for Interstitial Atomic Oxygen Content of Silicon by Infrared Absorption." Preferably, the same FTIR process is used to determine the concentration of oxygen and the absorbance of N—O complexes.

The selection of using N—O complexes to determine the concentration of nitrogen is due, at least in part, to the fact that their IR absorption peaks, or signals, are relatively easy to distinguish over the noise and absorption signals of other elements, whereas the IR absorption signals of N—N are difficult to distinguish because of their small maximum absorbance and because of interference from elements such as oxygen.

The use of N—O complexes, however, is not without difficulty. Specifically, determining the value of total nitrogen from the IR signal of a nitrogen reaction product (i.e., N—O complexes) requires reliably correlating measured IR absorption signals from the N—O reaction product with the actual concentration of nitrogen in the sample. To accomplish this, the method of the present invention comprises thermally annealing the sample to obtain a stable concentration of N—O which is in a fixed relationship to the total nitrogen content. Stated another way, the thermal anneal is performed in such a manner so as to reach a state of thermodynamic equilibrium among the various forms of nitrogen in silicon (e.g., molecular species, N—O complexes, and atomic species).

Figure 6:
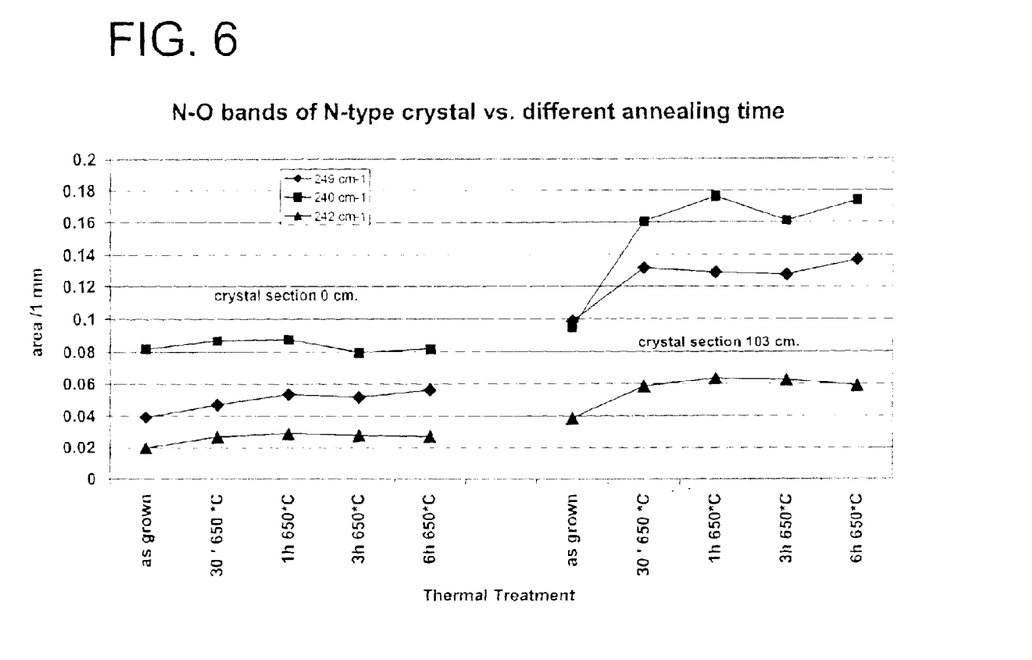
FIG. 6 is a graph of normalize absorption peak area versus annealing duration at about 650° C. for the absorption peaks at 240, 242 and 249 cm$^{-1}$ of the N-type silicon.

The thermodynamic equilibrium is preferably attained by annealing the sample at a temperature between about 500° C. and about 750° C. for a duration between about 2 minutes and about 290 hours. More preferably, themodynamic equilibrium is attained by annealing the sample at a temperature between about 600° C. and about 650° C. for a duration between about 30 minutes and about 4 hours. Increasing the temperature generally decreases the time required to reach N—O saturation and vice versa. For example, when annealing at a temperature of about 600° C., Hall measurements show a gradual increase of the nitrogen-related shallow thermal donors towards a saturation value which is reached after about 4 hours. See V. V. Voronkov et al., J. Appl. Phys. 89, 4289 (2001). Whereas, saturation can be reached in as little as about 30–40 minutes when the annealing is at about 650° C., as shown in FIG. 6. To assure that saturation of the N—O complexes is achieved, it may be desirable to exceed the minimum anneal duration, for example, when annealing at about 600° C. or 650° C., the duration my be extended to about 6 hours and about 1 hour, respectively.

In one embodiment of the present invention, the anneal temperature is selected as a function of a detection limit for the nitrogen-oxygen complexes. In other embodiment of the present invention, the anneal temperature is selected as a function of annealing time available to saturate the silicon sample with nitrogen-oxygen complexes. In yet another embodiment of the present invention, the annealing time is selected as a function of a detection limit for the nitrogen-oxygen complexes. An anneal temperature of about 650° C. is generally preferred over about 600° C. because it is the standard temperature for a thermal donor anneal and it allows saturation to be reached faster while maintaining a good sensitivity to nitrogen (i.e., the detection limit for nitrogen-oxygen complexes is low enough to measure the concentration of nitrogen in a sample at levels that were heretofore undetectable).

In instances where the nitrogen content in the silicon is low or conditions are otherwise such that the concentration of nitrogen in difficult to determine (e.g., although present, the concentration of N—O complexes is below the detection limit for the spectrometer being used), it is desirable to carry out the invention in such a way that increases the concentration of N—O complexes above the detection limit. This is generally accomplished by annealing the sample at a lower temperature (e.g., from about 550° C. to about 615° C.) for a longer duration. For any particular anneal temperature ($T_a$(° C.)) the minimum anneal duration ($t_{min}$) may be determined in accordance with the following equations:

$$t_{min}=0.5\ exp(2.5\ eV/k(T_a+273)-2.5\ eV/k(600+273))\text{hours.} \quad (3)$$

Although generally not as preferred, the method of the present invention may be performed by annealing the samples below about 600° C. or at temperatures greater than about 650° C. Generally, as annealing temperatures decrease from about 600° C., the concentration of N—O complexes tends to dramatically decrease and the concentration molecular nitrogen tends to increase unless the sample is annealed for relatively long periods (e.g., if $T_a$ is about 550° C., $t_{min}$ is about 30 hours and if $T_a$ is about 500° C., $t_{min}$ is about 290 hours). As annealing temperatures increase from about 800° C. to about 900° C., the concentration of N—O complexes is significantly reduced, and by about 1100° C., the N—O complexes are nearly completely eliminated.

Once the thermodynamic equilibrium is reached, the annealed silicon sample is subjected to Fourier Transform infrared spectroscopy over the spectral range corresponding to the electronic transition of the nitrogen-oxygen species over the far infrared spectral range of about 200 cm$^{-1}$ to about 300 cm$^{-1}$. Preferably, FTIR is performed while the sample is cooled to a temperature below about 20° K and more preferably to a temperature below about 15° K. This is typically accomplished using a cryostat and liquid helium. During the FTIR, the sample is also preferably illuminated with white light sufficient to yield stronger absorption peak area values than if performed without illumination. The white light illumination (e.g., about 100 W) eliminates the compensation due to donors (e.g., phosphorus and nitrogen) and acceptors (e.g., boron) by supplying enough energy to electrons and holes to avoid the combination and free movement. Although any N—O absorption peak may be measured and used to determine the concentration of nitrogen in a silicon sample, the preferred N—O absorption peaks occur at about 240 cm$^{-1}$ and/or about 249 cm$^{-1}$ because they are the most intense. Other absorption peaks associated with N—O complexes (e.g., at about 242 cm$^{-1}$ and about 246 cm$^{-1}$), are preferably not used to determine nitrogen concentration because they are significantly weaker and difficult to distinguish from the boron-related peak at about 245 cm$^{-1}$. Even more preferably, the concentration of nitrogen is determined by combining the 240 cm$^{-1}$ and the 249 cm$^{-1}$ absorption peak measurements because this maximizes the sensitivity of the measurement, especially at low concentrations which could result in one of the peaks being at or below the noise level while the other is detectable (i.e., using the sum is preferred because it includes all, or nearly all, of the N—O species). The measurement of the absorption peaks may be the area under the peak or the peak height. Preferably, the measurement is the peak area.

Each absorption peak measurement is preferably normalized by dividing the value (the peak area or the peak height) by the thickness of the sample (in millimeters) so that the normalized peak area is referred to in unit thickness (1 mm). This allows normalized peak measurements from different samples with varying thicknesses to be compared. The normalized peak measurements are used to determine the concentration of nitrogen in the sample using a calibration equation determined in accordance with the procedures set forth below.

Calibration Equations

A nitrogen-containing silicon crystal is grown by the CZ method by pulling the crystal from a melt prepared by adding silicon nitride to the polycrystalline silicon charge. The melt has a starting nitrogen concentration ($N_0^*$), and as a silicon crystal is pulled from the melt, nitrogen is segregated to the melt. The segregation coefficient (K) of nitrogen in silicon is low: $K=7\times10^{-4}$ (almost all nitrogen is segregated to the melt during crystal growth). Accordingly, the nitrogen concentration in the melt (N*) increases with the increasing solid fraction (g) and the nitrogen concentration in the solid, N=KN*, follows this variation:

$$N=KN_0^*/(1-g). \quad (4)$$

Typically, the concentration of nitrogen increases by a factor of about 5 from the seed end to the tail end of the crystal. The accuracy of the foregoing equation was confirmed by SIMS.

Using the foregoing nitrogen segregation equation, a theoretical concentration of nitrogen for a sample is determined. The area under the peak determined by LT-FTIR for the sample is determined. Thus, a relationship between the peak height or peak area and the nitrogen concentration for a sample is established. This process is performed for several samples at varying nitrogen concentrations (i.e., samples are taken at different positions along the length of the ingot) to produce a plot of points correlating peak area and nitrogen concentration. The best fit line equation of the plot is the calibration equation.

Figure 4A:
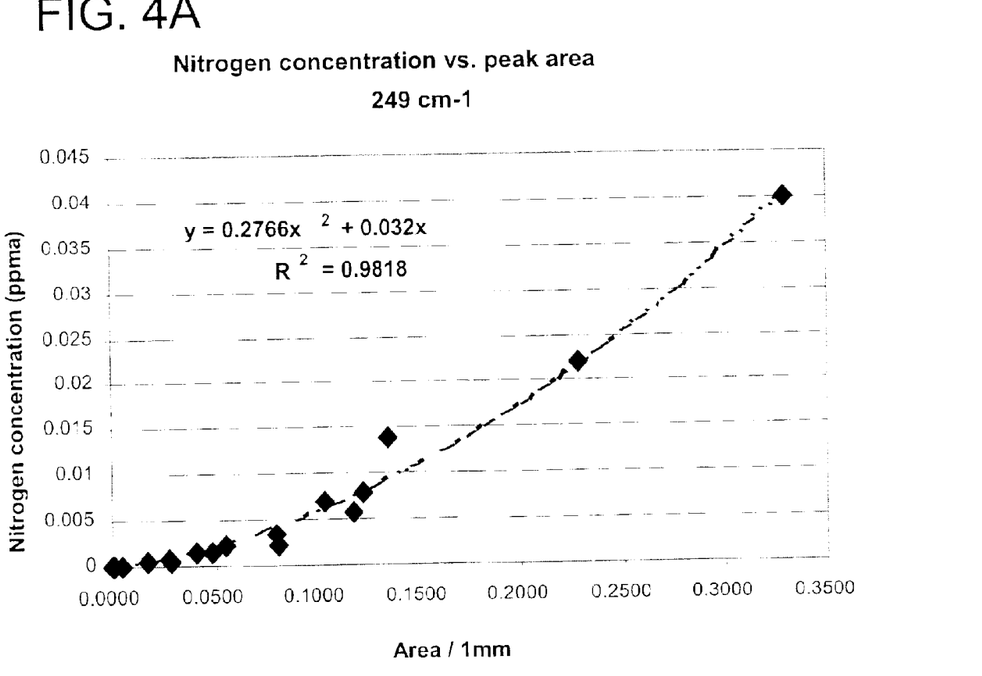
FIGS. 4a, 4b and 4c are plots correlating the calculated nitrogen concentration (using a segregation coefficient of 0.0007) and normalized absorption peak areas for the 240, 249 cm$^{-1}$ peaks and for the sum of the two absorption peak areas for all the samples annealed at about 650° C. for about 30 minutes.
Figure 4B:
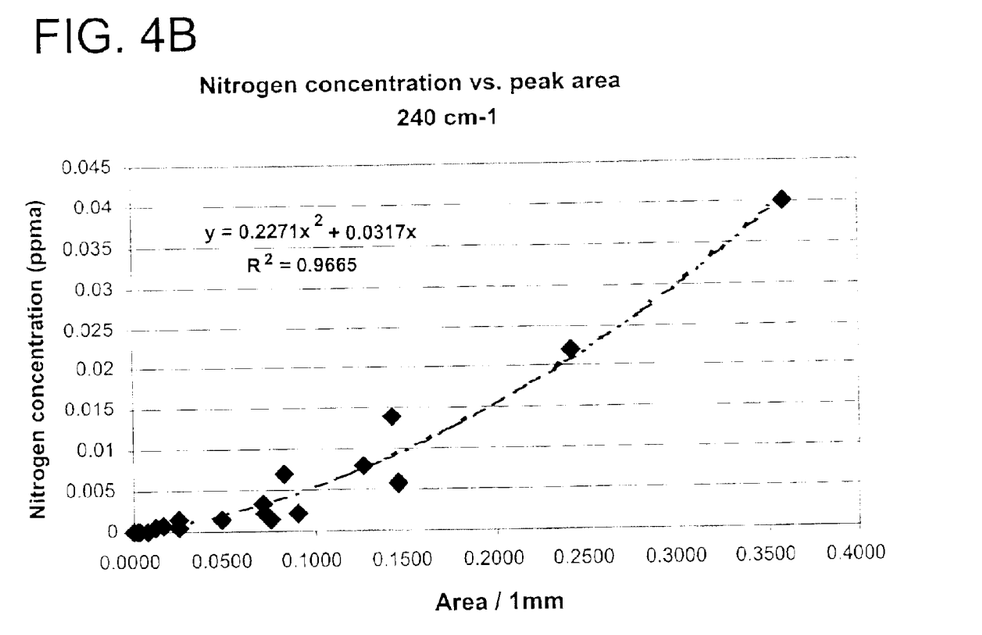
Figure 4C:
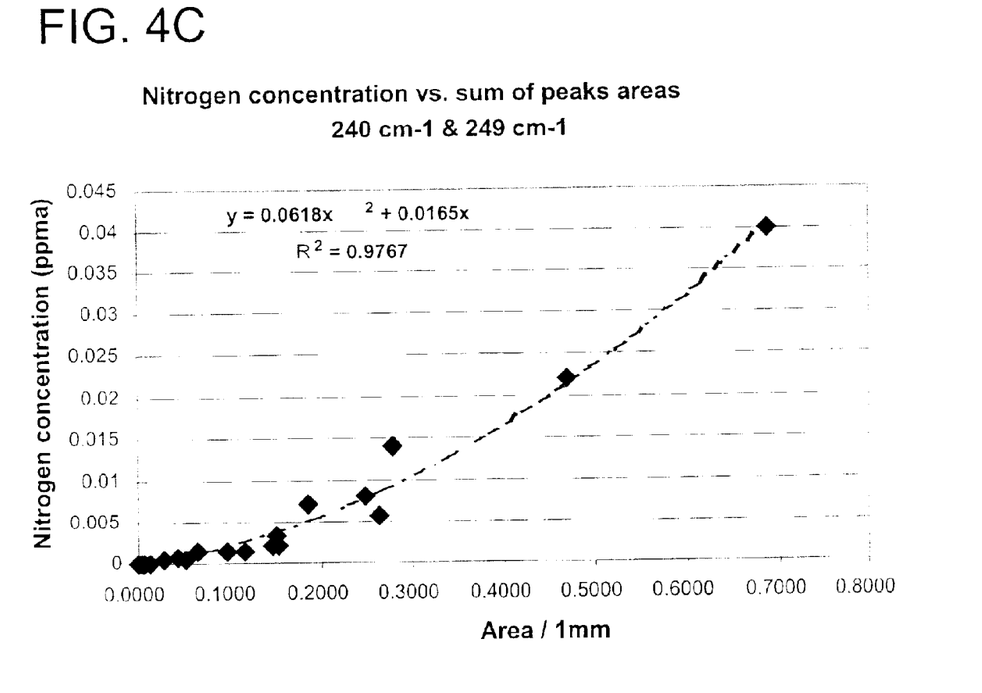

For silicon samples comprising about $7\times10^{17}$ oxygen atoms/cm$^3$ that were annealed at about 650° C. for about 30 minutes, the following calibration equations have been determined using the plots of FIGS. 4a, 4b and 4c:

$$N(ppma)=0.2271A_1^2+0.0317A_1; \quad (5)$$

$$N(ppma)=0.2766A_2^2+0.032A_2; \quad (6)$$

and $$N(ppma)=0.0618(A_1+A_2)^2+0.0165(A_1+A_2). \quad (7)$$

$A_1$ is the normalized peak area of the 240 cm$^{-1}$ absorption band, and $A_2$ is the normalized peak area of the 249 cm$^{-1}$ absorption band. The regression coefficients of the calibration equations are 0.967, 0.982 and 0.977, respectively.

The above equations ($2^{nd}$ order polynomials) follow directly from the equilibrium condition between total nitrogen concentration and the concentration of optically active species set forth by V. V. Voronkov et al. in an article published in the Journal of Applied Physics 89, 4289 (2001) which is hereby incorporated by reference in its entirety. The relationship between nitrogen concentration and peak area is non-linear. This is due to the fact that the peak area is proportional to the concentration of the nitrogen-oxygen complexes, which, in turn, is proportional not to the total nitrogen concentration, but to the square root of the total nitrogen concentration. See V. V. Voronkov et al., J. Appl. Phys. 89, 4289 (2001).

As stated above, the foregoing calibration equations are specific for samples having a particular oxygen concentration ($7 \times 10^{17}$ atoms/cm$^3$) and a particular anneal temperature (650° C.). If a sample has a different oxygen concentration and/or a different anneal temperature is desired, new calibration equations are created in accordance with the procedures set forth above or a correction factor (Z) is applied to the foregoing calibration equations. The mass-action law relation between the total nitrogen concentration (N) and N—O complexes ($N_S$) is as follows:

$$N_S^2/(N-N_S)=R. \quad (8)$$

The coefficient R (a mass-law constant) is dependent on the anneal temperature and oxygen concentration, and for an oxygen concentration of $7 \times 10^{17}$ atoms/cm$^3$:

$$R=9.74 \times 10^{-4} \exp(3.02 \ eV/k(T_a+273)). \quad (9)$$

Because coefficient R depends on the oxygen concentration of the sample, if the oxygen concentration of the sample is different than the samples used to create the calibration equation, the coefficient R is adjusted using an approximated power law, $O_i^q$, where the exponent q is estimated to be about 5.5. As a result, the calibration adjustment factor (Z) is as follows:

$$Z=R_{adjust}/R=(O_i/7 \times 10^{17})^{5.5} \exp(3.02/k(T_a+273)-3.02/k(650+273)). \quad (10)$$

Thus, the calibration equations may be adjusted using the calibration adjustment factor (Z), as follows:

$$N(ppma)=(0.2271/Z)A_1^2+0.0317A_1; \quad (11)$$

$$N(ppma)=(0.2766/Z)A_2^2+0.032A_2; \quad (12)$$

and $$N(ppma)=(0.0618/Z)(A_1+A_2)^2+0.0165(A_1+A_2). \quad (13)$$

EXAMPLES

Equipment

The following equipment was used to evaluate nitrogen in silicon in accordance with the method of the present invention. The LT-FTIR spectrometer was a BRUKER IFS 66 V with a CRYOVAC cryostat using liquid helium to reduce the sample temperature to below about 15° K. The LT-FTIR was set to scan the spectral range between about 190 and about 1200 cm$^{-1}$. A PERKIN-ELMER PARAGON infrared spectrometer was used to analyze silicon samples in the middle infrared range at room temperature. A standard silicon wafer production furnace was used to anneal the silicon samples.

Sample Preparation

The samples of single crystal silicon crystal were taken from CZ and FZ grown ingots that were undoped or doped with amounts of nitrogen. Additionally, both P-type and N-type CZ ingots were grown.

The FZ rods were prepared from the same polycrystalline silicon lot and refined under an argon atmosphere with certified levels of nitrogen (0%, 0.5%, 1% and 3% nitrogen by volume). Samples having a thickness of about 9 mm were prepared from the seed end and the tail end of the rods and were double side etch-polished.

The CZ samples were cut from crystals having different nitrogen doping concentrations, target resistivities and average interstitial oxygen concentrations. The characteristics of the CZ crystals are set forth in Table 1 below.

TABLE 1

| Crystal | N concentration in the melt (ppma) | Target Resistivity (ohm · cm) | Average Oi (ppma) |
|---|---|---|---|
| 412 AG | 0 | 70 P-type | 15.0 |
| 412 AH | 2.0 | 70 P-type | 15.0 |
| 811 EP | 20.0 | 70 P-type | 15.0 |
| 070 GH | 2.0 | 43 P-type | 14.0 |

Three samples having a thickness of about 5 mm were taken from the seed end, at about the middle of the ingot (about 50 cm from the seed end), and at the tail end. One sample from each location of each crystal was either annealed at about 650° C. for about 30 minutes, annealed at 900° C. for about 5 minutes, or left "as grown" (i.e., not annealed). The samples were then double side etch-polished. Additionally, to study the impact of anneal duration on the N—O complexes absorption peaks, samples were taken from the N-type ingot and annealed at about 650° C. for a duration of about 0.5, 1, 3 or 6 hours prior to being subjected to LT-FTIR in the far infrared spectral range.

A second set of CZ crystals were grown to further explore the nitrogen range between 0 and 2 ppma. Their characteristics are summarized in Table 2.

TABLE 2

| Crystal | N concentration in the melt (ppma) | Target Resistivity (ohm · cm) | Average Oi (ppma) |
|---|---|---|---|
| 413 DC | 0.15 | 70 P-type | 14.2 |
| 413 CY | 0.5 | 70 P-type | 14.2 |
| 413 DL | 1.0 | 70 P-type | 14.3 |
| 413 CW | 2.0 | 25 P-type | 12.6 |

Samples were taken from the seed and tail ends of the crystals, annealed at about 650° C. for about 30 minutes, and double side etch-polished.

Results and Discussion

Float Zone Samples

In the middle infrared spectral range, the two absorption peaks characteristic of N—N bonds at 960 and 766 cm$^{-1}$ were detected at room temperature for the FZ rod refined under 3% nitrogen atmosphere (at the seed end and the tail end) and under 1% nitrogen atmosphere (at the tail end). The intensity of the absorption lines is rather low (maximum absorbance is 0.018 in the tail end sample of the rod doped with a 3% nitrogen atmosphere). In all the remaining samples, no absorption peaks were detected at 960 or 766 cm$^{-1}$. Performing the FTIR at a temperature below about 15° K did not increase improve the sensitivity in agreement with P. Wagner, R. Oeder and W. Zulehner, Appl. Phys. A 46 (1988) p. 73. Table 3 contains the measurement results of all samples for the 963 cm$^{-1}$ absorption peak together with the estimated nitrogen concentration determined using Equation (1).

TABLE 3

| Sample | Normalized Absorbance at Peak 963 cm$^{-1}$ | Calculate N concentration (atoms/cm$^3$) | Calculate N concentration (ppba) |
|---|---|---|---|
| 0% N2 | 0 | 0 | 0 |
| 3% N2 seed end | 0.0056 | 2.4 × 1015 | 48 |
| 3% N2 tail end | 0.0147 | 6.2 × 1015 | 125 |
| 1% N2 seed end | <0.001 | <0.5 × 1015 | <10 |
| 1% N2 tail end | ca 0.0023 | ca 1 × 1015 | ca 20 |
| 0.5% N2 seed end | <0.001 | <0.5 × 1015 | <10 |
| 0.5% N2 tail end | <0.001 | <0.5 × 1015 | <10 |

The minimum detectable absorbance was about 0.001 which corresponds to a nitrogen concentration of about $0.5 \times 10^{15}$ atoms/cm$^3$ which can be considered to be the detection limit for FTIR in the middle infrared spectral range. This detection limit is sufficient for quality control of incoming polysilicon because a nitrogen concentration of $0.5 \times 10^{15}$ atoms/cm$^3$ corresponds to a concentration of about $10^{12}$ atoms/cm$^3$ at the crystal tail end. In the far infrared spectral range, no nitrogen-related peaks were observed which was consistent with expectations (i.e., because of the extremely low oxygen concentration in FZ silicon there are not any detectable peaks for N—O complexes).

Czochralski Samples

In the middle infrared spectral range, the CZ samples, in contrast to the FZ samples, did not show any significant nitrogen-related absorption peak even at the highest nitrogen concentration (i.e., ca $3 \times 10^{15}$ atoms/cm$^3$ of sample 811 EP at the tail end) for any thermal treatment (as-grown, 650° C. for 30 minutes, and 900° C. for 5 minutes), or measurement temperature (room temperature or 15° K). It is presently believed that this is due primarily to the fact that the nitrogen has reacted with oxygen and is no longer present as the molecular species. In the far infrared spectral range, on the other hand, all nitrogen-doped samples show several clear absorption peaks within the 180–280 cm$^{-1}$ range that are attributable to N—O complexes. See X. H. Shi et al, Sol. Sate Comm., vol. 106, 10, p. 669–671 (1998). In particular, the intensities of the 240, 242 and 249 cm$^{-1}$ peaks are quite high. Further, the 240 and 249 cm$^{-1}$ peaks are of particular interest because there is less interference with the 245 cm$^{-1}$ peak associated with boron.

Figure 1A:
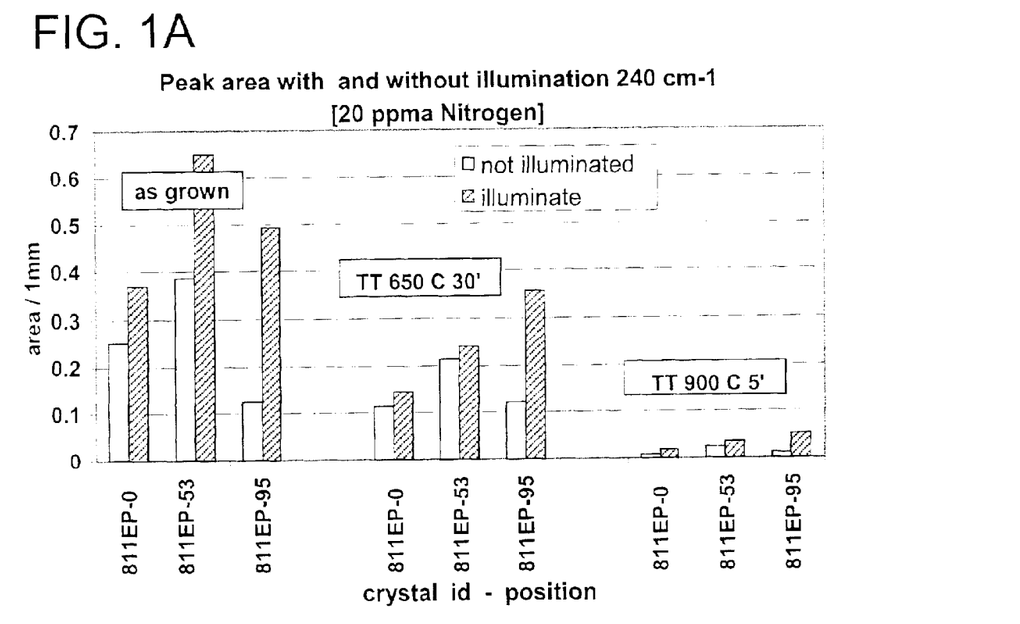
FIGS. 1a and 1b are graphs of the normalized absorption peak area for crystal 811 EP (20 ppma nitrogen doping) at 240 and 249 cm$^{-1}$, respectively.
Figure 1B:
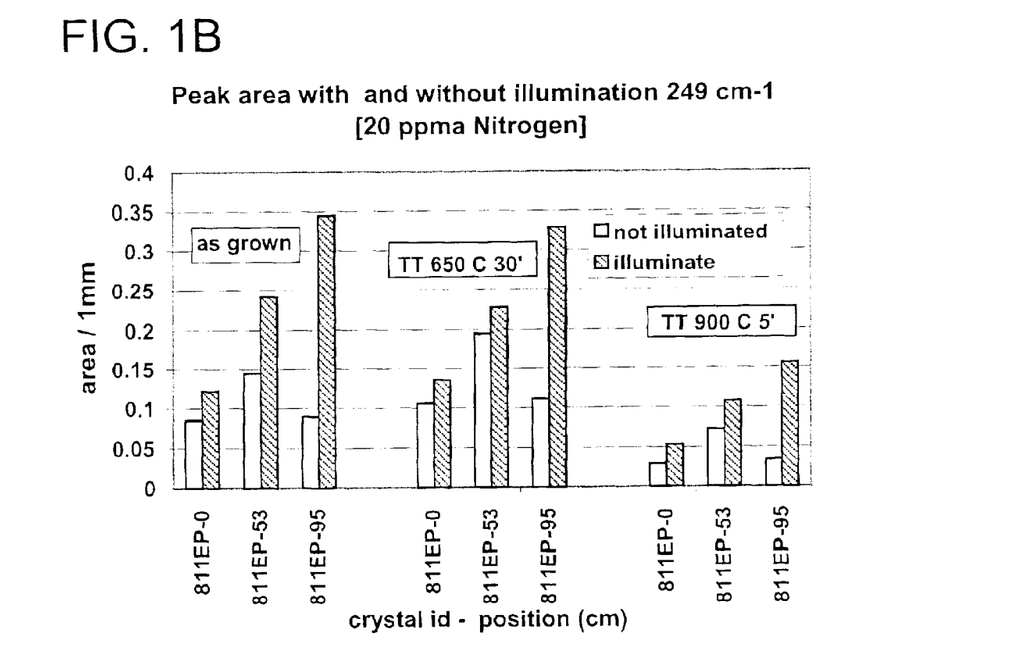
Figure 2A:
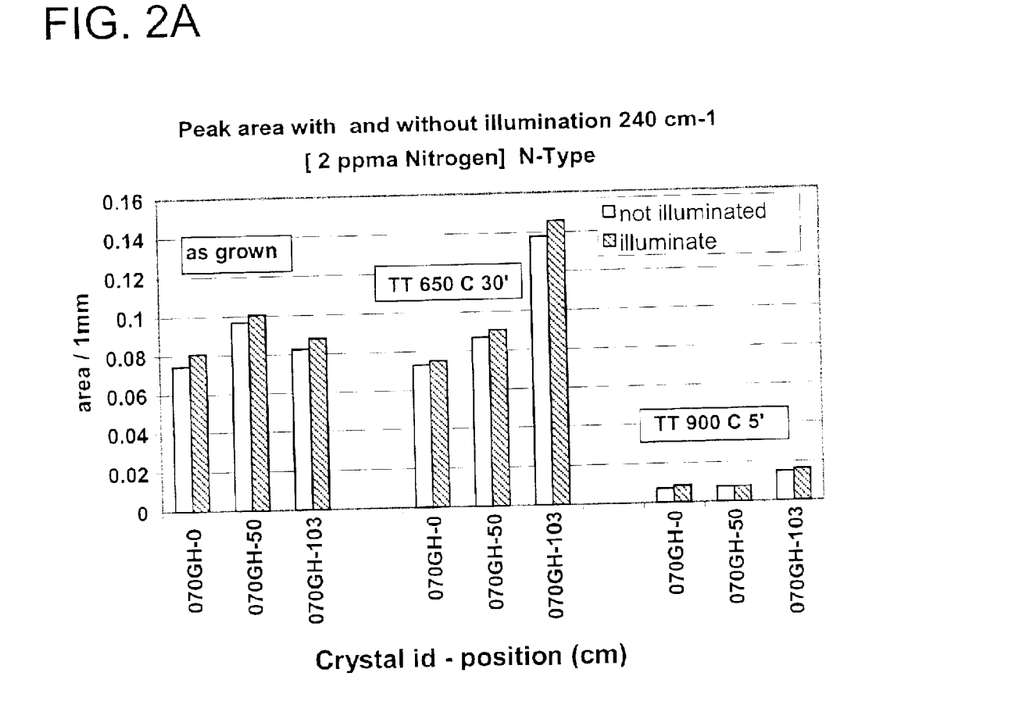
FIGS. 2a and 2b are graphs of the normalized absorption peak area for crystal 412 AH (2 ppma nitrogen doping) at 240 and 249 cm$^{-1}$, respectively.
Figure 2B:
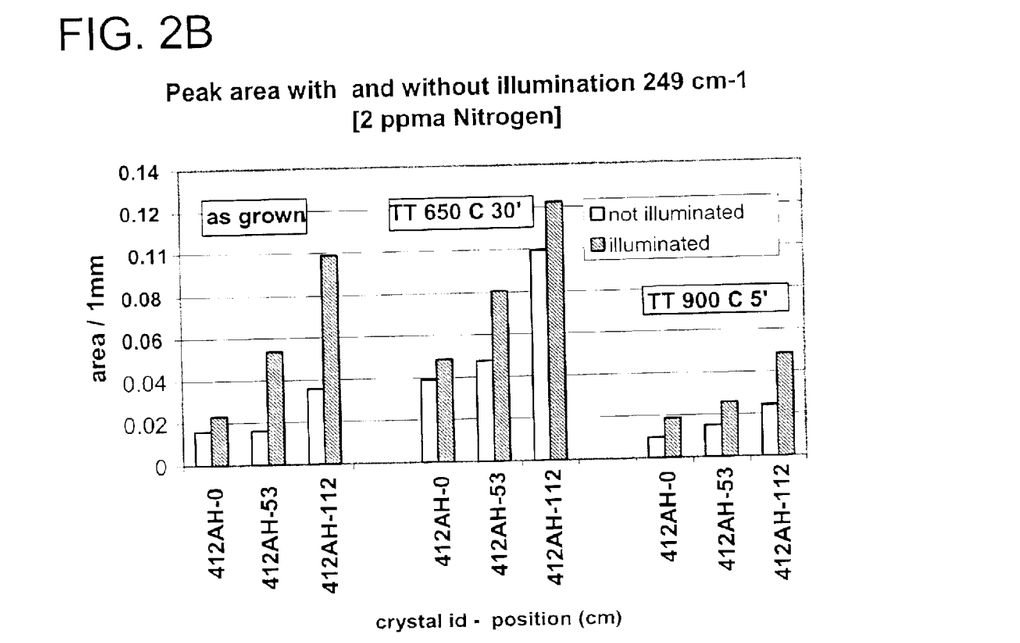

FIGS. 1a and 1b are graphs of the normalized absorption peak area for crystal 811 EP (20 ppma nitrogen doping) at 240 and 249 cm$^{-1}$, respectively. FIGS. 2a and 2b are graphs of the normalized absorption peak area for crystal 412 AH (2 ppma nitrogen doping) at 240 and 249 cm$^{-1}$, respectively. The reference crystal 412 AG (0 ppma nitrogen) did not have any detectable nitrogen-related peaks. Referring to FIGS. 1 and 2, the following observations were made. First, measurements performed with sample illumination provide higher peak area values than those performed without illumination, and show an axial nitrogen concentration trend which is consistent with expectations, especially for annealed samples. This is due to the fact that illumination eliminates the compensation due to donors and acceptors present in the sample. See DIN 50438-3, Bestimmung des Verunreinigungsgehaltes in Silicium mittels infrarot-absorption teil 3 Bor und Phosphor. Second, in the as-grown samples the axial nitrogen concentration trend is not consistent with settled expectations (i.e., the nitrogen concentration steadily increases toward the tail end during ingot growth), even with illumination. It is presently believed that this is due to the varying thermal history of the ingot during growth (i.e., the tail end spends less time is spent in the N—O complex formation temperature range, around 600° C., during crystal growth). Third, although clearly detectable with a reasonable axial trend, the absorption peaks are substantially reduced after annealing at about 900° C. for about 5 minutes.

Figure 3A:
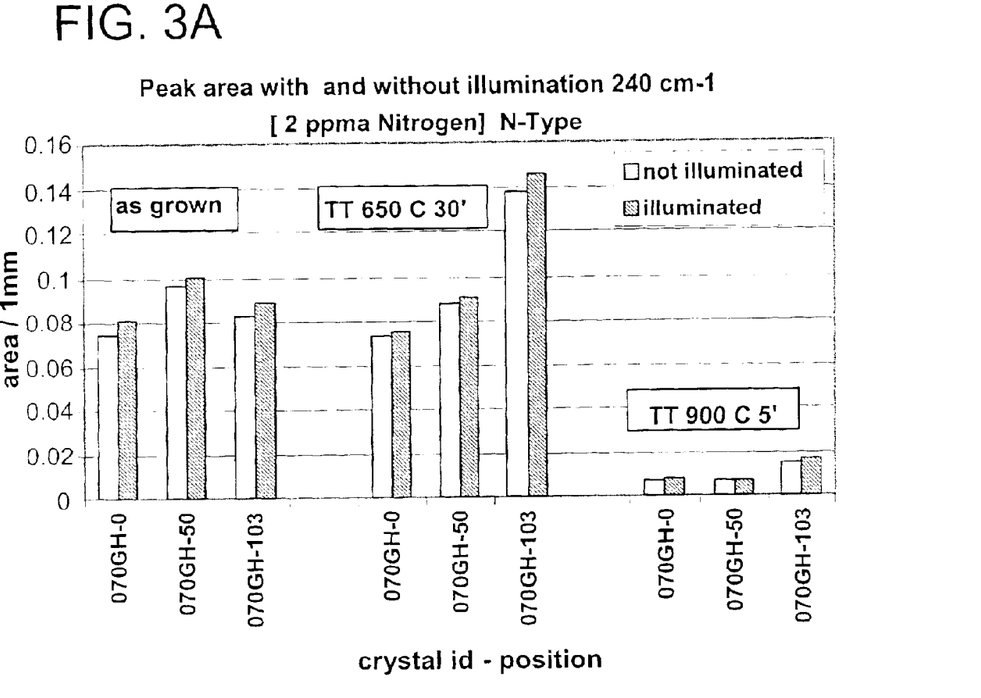
FIGS. 3a, 3b and 3c are graphs of the normalized absorption peak area for the N-type crystal samples doped with 2 ppma nitrogen in the melt at 240, 242 and 249 cm$^{-1}$, respectively.
Figure 3B:
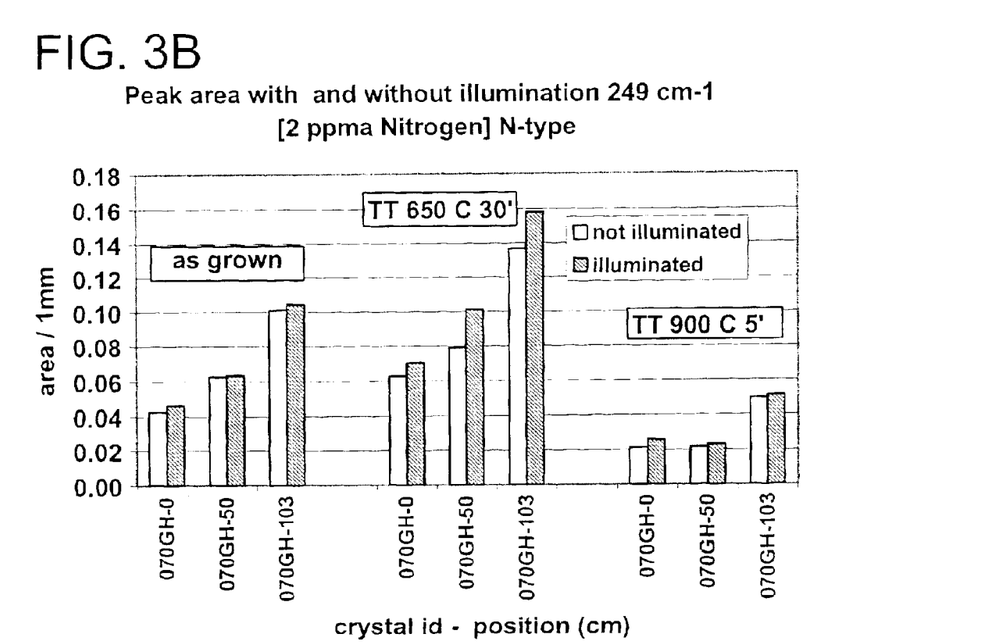
Figure 3C:
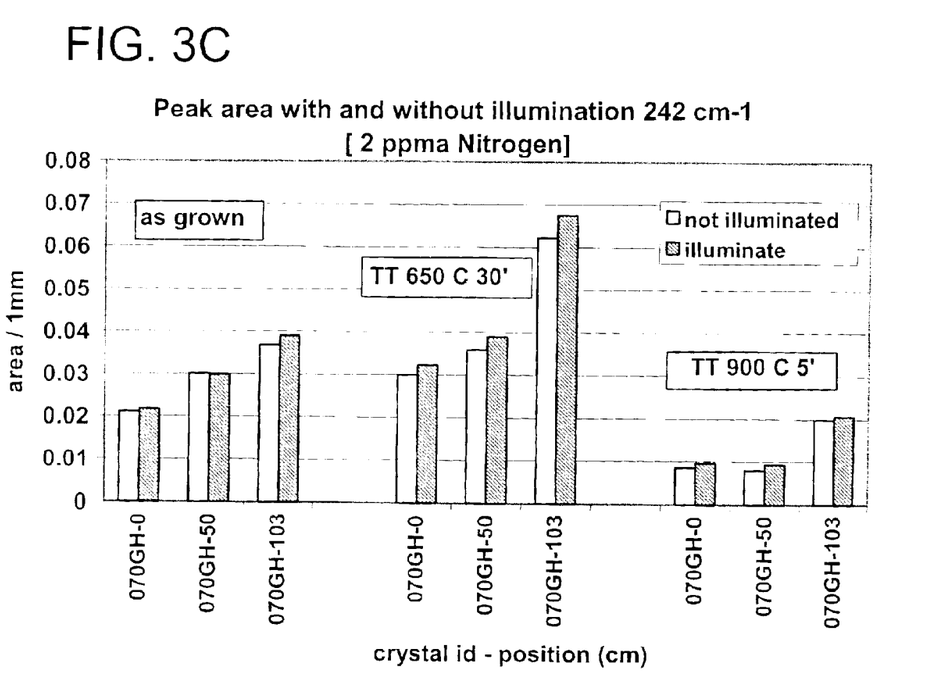

FIGS. 3a, 3b, and 3c are graphs of the normalized absorption peak area for the N-type crystal samples doped with 2 ppma nitrogen in the melt at 240, 242 and 249 cm$^{-1}$, respectively. In the N-type silicon, the 242 cm$^{-1}$ peak is well resolved because of less interference from the 245 cm$^{-1}$ boron peak. The intensities of the 240 and 249 cm$^{-1}$ peaks are slightly higher for the N-type samples than for the P-type samples with the same nitrogen doping level; this may merely be due to process and measurement variability.

FIGS. 4a, 4b, and 4c are plots correlating the calculated nitrogen concentration (using a nitrogen segregation coefficient of $7 \times 10^{-4}$) and normalized absorption peak areas for the 240, 249 cm$^{-1}$ peaks and for the sum of the two absorption peak areas for all the samples annealed at about 650° C. for about 30 minutes. The following observations were made. The relationship between nitrogen concentration and peak area is non-linear which is due to the fact that the peak area is proportional to the concentration of N—O complexes, which, in turn, is proportional not to the total nitrogen concentration, but to the square root of nitrogen. See V. V. Voronkov et al., J. Appl. Phys. 89,4289 (2001). The correlation coefficient $R^2$ between the calculated nitrogen concentration and measured peak areas is greater than 0.966 for all three wavelengths. Thus, either the 240 cm$^{-1}$ or 249 cm$^{-1}$ peak or their sum may be used to measure the concentration of nitrogen in silicon, however, the sum of the two is preferred to maximize the sensitivity of the measurement especially at low concentration where one of the lines could be at or below the noise level and the other detectable.

Figure 5:
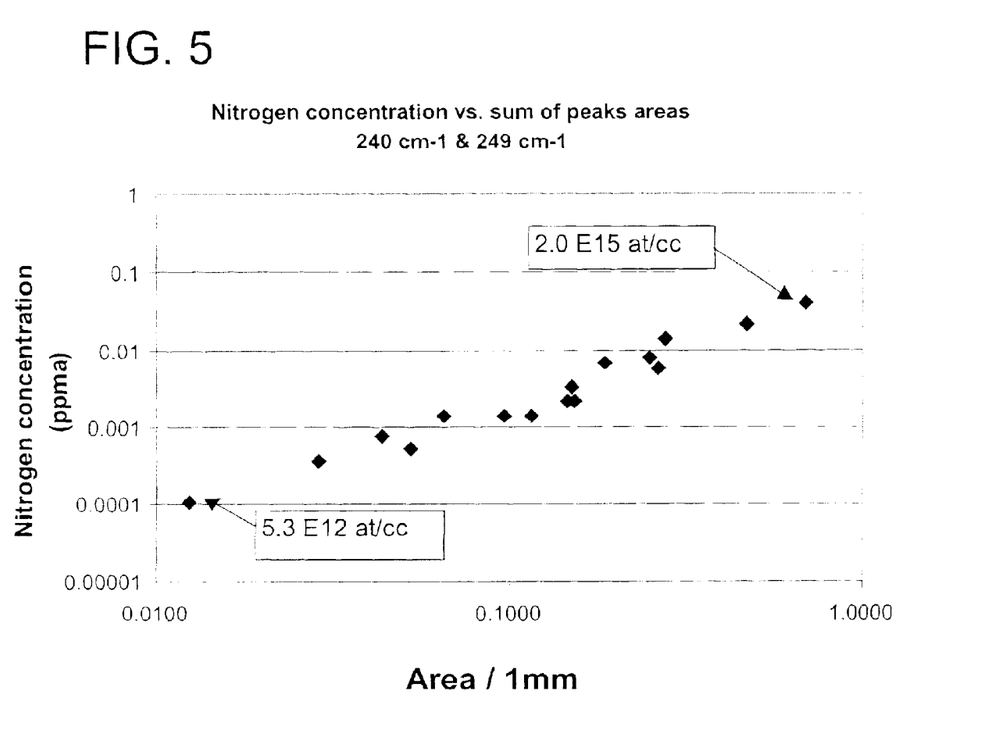
FIG. 5 is a plot of the data in FIG. 4 on a logarithmic scale to highlight the measurement behavior at the very low nitrogen concentrations.

FIG. 5 is a plot of the data in FIG. 4 on a logarithmic scale to highlight the measurement behavior at the very low nitrogen concentrations. As can be seen, the correlation is good even at the lowest detected nitrogen concentration—about $5.3 \times 10^{12}$ atoms/cm$^3$ which corresponds to a normalized peak area sum of about 0.0124. The minimum detectable peak area under the experimental conditions was estimated to about 0.01 which corresponds to a detection limit for nitrogen of about $5 \times 10^{12}$ atoms/cm$^3$ or 0.1 ppba. This detection limit is at least one order of magnitude lower than the best detection limit achievable with SIMS (~$10^{14}$ atoms/cm$^3$).

The explanations and illustrations presented herein and in the Appendices are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A method for measuring a concentration of nitrogen in a silicon sample by Fourier Transform infrared spectroscopy, the method comprising:

annealing the silicon sample at an annealing temperature $T_a$ for an annealing time $t_a$ to saturate the silicon sample with nitrogen-oxygen complexes;

performing Fourier Transform infrared spectroscopy to measure an absorbance value related to the concentration of nitrogen-oxygen complexes in the annealed silicon sample; and calibrating the absorbance value to a nitrogen concentration value.

2. The method of claim 1 wherein in $T_a$ is between about 500° C. and about 750° C.

3. The method of claim 1 wherein $T_a$ is an annealing temperature which results in saturation of the silicon sample with nitrogen-oxygen complexes for an annealing time $t_a$ that is between about 2 minutes and about 290 hours.

4. The method of claim 1 wherein $T_a$ is between about 600° C. to about 650° C. and $t_a$ is between about 0.5 hours to about 4 hours.

5. The method of claim 1 wherein $T_a$ is selected as a function of a detection limit for the nitrogen-oxygen complexes and as a function of annealing time available to saturate the silicon sample with nitrogen-oxygen complexes.

6. The method of claim 1 comprising:
measuring an interstitial oxygen concentration of the silicon;
calculating a calibration adjustment factor as a function of said initial oxygen concentration; and
calibrating the absorbance value to the nitrogen concentration value using said calibration adjustment factor.

7. The method of claim 1 comprising:
measuring an interstitial oxygen concentration of the sample;
calculating a calibration adjustment factor as a function of said initial oxygen concentration and said annealing temperature; and
calibrating the absorbance value to the nitrogen concentration value using said calibration adjustment factor.

8. The method of claim 1 wherein the Fourier Transform infrared spectroscopy is performed while illuminating the silicon sample with white light to eliminate compensation due to donors and acceptors.

9. The method of claim 1 wherein the absorbance value comprises a value selected from among values consisting of a height corresponding to an absorption band at about 240 $cm^{-1}$, an area corresponding to an absorption band at about 240 $cm^{-1}$, and a combination thereof.

10. The method of claim 1 wherein the absorbance value comprises a value selected from among values consisting of a height corresponding to an absorption band at about 249 $cm^{-1}$, an area corresponding to an absorption band at about 249 $cm^{-1}$, and a combination thereof.

11. The method of claim 1 wherein:
the absorbance value measured is selected from values consisting of a first area under a first FTIR absorbance band for nitrogen-oxygen complexes, a second area under a second FTIR absorbance band for nitrogen-oxygen complexes, and a sum of said first area and said second area; and
the calibrating the absorbance value to the nitrogen concentration value is achieved using an equation selected as a function of which said values are selected for said absorbance value.

12. The method of claim 1 wherein:
the absorbance value measured is a first area $A_1$, in units of $cm^{-2}$, under a first FTIR absorbance band at about 240 $cm^{-1}$; and
the calibrating the absorbance value to the nitrogen concentration value is achieved using an equation as follows:

$$N(ppma)=(0.2271/Z)A_1^2+0.0317A_1$$

wherein Z is a calibration adjustment factor calculated as a function of an interstital oxygen concentration of the sample and said annealing temperature.

13. The method of claim 1 wherein:
the absorbance value measured is a second area $A_2$ in units of $cm^{-2}$, under a second FTIR absorbance band at about 249 $cm^{-1}$; and
the calibrating the absorbance value to the nitrogen concentration value is achieved using an equation as follows:

$$N(ppma)=(0.2766/Z)A_2^2+0.032A_2$$

wherein Z is a calibration adjustment factor calculated as a function of an interstital oxygen concentration of the sample and said annealing temperature.

14. The method of claim 1 wherein:
the absorbance value measured is a first area $A_1$, in units of $cm^{-2}$, under a first FTIR absorbance band at about 240 $cm^{-1}$ and a second area $A_2$, in units of $cm^{-2}$, under a second FTIR absorbance band at about 249 $cm^{-1}$; and
the calibrating the absorbance value to the nitrogen concentration value is achieved using an equation as follows:

$$N(ppma)=(0.0618/Z)(A_1+A_2)^2+0.0165(A_1+A_2)$$

wherein Z is a calibration adjustment factor calculated as a function of an interstital oxygen concentration of the sample and said annealing temperature.

15. The method of claim 1 comprising normalizing the absorbance value to a standard thickness prior to calibrating the absorbance value to the nitrogen concentration value.

16. A method for measuring a concentration of nitrogen in a silicon sample by Fourier Transform infrared spectroscopy, the method comprising:
annealing the silicon sample at an annealing temperature $T_a$ for an annealing time $t_a$ to saturate the silicon sample with nitrogen-oxygen complexes, wherein $T_a$ is selected as a function of a detection limit for the nitrogen-oxygen complexes;
performing Fourier Transform infrared spectroscopy to measure an absorbance value related to the concentration of nitrogen-oxygen complexes in the annealed silicon sample; and
calibrating the absorbance value to a nitrogen concentration value.

17. The method of claim 16 wherein in $T_a$ is between about 500° C. and about 750° C.

18. The method of claim 16 wherein $T_a$ is an annealing temperature which results in saturation of the silicon sample with nitrogen-oxygen complexes for an annealing time $t_a$ that is between about 2 minutes and about 290 hours.

19. The method of claim 16 wherein $T_a$ is between about 600° C. to about 650° C. and $t_a$ is between about 0.5 hours to about 4 hours.

20. The method of claim 16 comprising:
measuring an interstitial oxygen concentration of the silicon;
calculating a calibration adjustment factor as a function of said initial oxygen concentration; and
calibrating the absorbance value to the nitrogen concentration value using said calibration adjustment factor.

21. The method of claim 16 comprising:
measuring an interstitial oxygen concentration of the sample;
calculating a calibration adjustment factor as a function of said initial oxygen concentration and said annealing temperature; and
calibrating the absorbance value to the nitrogen concentration value using said calibration adjustment factor.

22. The method of claim 16 wherein the Fourier Transform infrared spectroscopy is performed while illuminating the silicon sample with white light to eliminate compensation due to donors and acceptors.

23. The method of claim 16 wherein the absorbance value comprises a value selected from among values consisting of a height corresponding to an absorption band at about 240 $cm^{-1}$, an area corresponding to an absorption band at about 240 $cm^{-1}$, and a combination thereof.

24. The method of claim 16 wherein the absorbance value comprises a value selected from among values consisting of a height corresponding to an absorption band at about 249 cm$^{-1}$, an area corresponding to an absorption band at about 249 cm$^{-1}$, and a combination thereof.

25. The method of claim 16 wherein:
the absorbance value measured is selected from values consisting of a first area under a first FTIR absorbance band for nitrogen-oxygen complexes, a second area under a second FTIR absorbance band for nitrogen-oxygen complexes, and a sum of said first area and said second area; and
the calibrating the absorbance value to the nitrogen concentration value is achieved using an equation selected as a function of which said values are selected for said absorbance value.

26. The method of claim 16 wherein:
the absorbance value measured is a first area $A_1$, in units of cm$^{-2}$, under a first FTIR absorbance band at about 240 cm$^{-1}$; and
the calibrating the absorbance value to the nitrogen concentration value is achieved using an equation as follows:

$$N(ppma)=(0.2271/Z)A_1^2+0.0317A_1$$

wherein Z is a calibration adjustment factor calculated as a function of an interstitial oxygen concentration of the sample and said annealing temperature.

27. The method of claim 16 wherein:
the absorbance value measured is a second area $A_2$, in units of cm$^{-2}$, under a second FTIR absorbance band at about 249 cm$^{-1}$; and
the calibrating the absorbance value to the nitrogen concentration value is achieved using an equation as follows:

$$N(ppma)=(0.2766/Z)A_2^2+0.032A_2$$

wherein Z is a calibration adjustment factor calculated as a function of an interstital oxygen concentration of the sample and said annealing temperature.

28. The method of claim 16 wherein:
the absorbance value measured is a first area $A_1$, in units of cm$^{-2}$, under a first FTIR absorbance band at about 240 cm$^{-1}$ and a second area $A_2$, in units of cm$^{-2}$, under a second FTIR absorbance band at about 249 cm$^{-1}$; and
the calibrating the absorbance value to the nitrogen concentration value is achieved using an equation as follows:

$$N(ppma)=(0.0618/Z)(A_1+A_2)^2+0.0165(A_1+A_2)$$

wherein Z is a calibration adjustment factor calculated as a function of an interstitial oxygen concentration of the sample and said annealing temperature.

29. The method of claim 16 comprising normalizing the absorbance value to a standard thickness prior to calibrating the absorbance value to the nitrogen concentration value.

30. A method for detecting a measurement of concentration of nitrogen in a silicon sample by Fourier Transform infrared spectroscopy, the method comprising:
annealing the silicon sample at an annealing temperature $T_a$ for an annealing time $t_a$ to saturate the silicon sample with nitrogen-oxygen complexes, wherein $T_a$ is selected as a function of annealing time available to saturate the silicon sample with nitrogen-oxygen complexes;
performing Fourier Transform infrared spectroscopy to measure an absorbance value related to the concentration of nitrogen-oxygen complexes in the annealed silicon sample; and
calibrating the absorbance value to a nitrogen concentration value.

31. The method of claim 30 wherein in $T_a$ is between about 500° C. and about 750° C.

32. The method of claim 30 wherein $T_a$ is an annealing temperature which results in saturation of the silicon sample with nitrogen-oxygen complexes for an annealing time $t_a$ that is between about 2 minutes and about 290 hours.

33. The method of claim 30 wherein $T_a$ is between about 600° C. to about 650° C. and $t_a$ is between about 0.5 hours to about 4 hours.

34. The method of claim 30 comprising:
measuring an interstitial oxygen concentration of the silicon;
calculating a calibration adjustment factor as a function of said initial oxygen concentration; and
calibrating the absorbance value to the nitrogen concentration value using said calibration adjustment factor.

35. The method of claim 30 comprising:
measuring an interstitial oxygen concentration of the sample;
calculating a calibration adjustment factor as a function of said initial oxygen concentration and said annealing temperature; and
calibrating the absorbance value to the nitrogen concentration value using said calibration adjustment factor.

36. The method of claim 30 wherein the Fourier Transform infrared spectroscopy is performed while illuminating the silicon sample with white light to eliminate compensation due to donors and acceptors.

37. The method of claim 30 wherein the absorbance value comprises a value selected from among values consisting of a height corresponding to an absorption band at about 240 cm$^{-1}$, an area corresponding to an absorption band at about 240 cm$^{-1}$, and a combination thereof.

38. The method of claim 30 wherein the absorbance value comprises a value selected from among values consisting of a height corresponding to an absorption band at about 249 cm$^{-1}$, an area corresponding to an absorption band at about 249 cm$^{-1}$, and a combination thereof.

39. The method of claim 30 wherein:
the absorbance value measured is selected from values consisting of a first area under a first FTIR absorbance band for nitrogen-oxygen complexes, a second area under a second FTIR absorbance band for nitrogen-oxygen complexes, and a sum of said first area and said second area; and
the calibrating the absorbance value to the nitrogen concentration value is achieved using an equation selected as a function of which said values are selected for said absorbance value.

40. The method of claim 30 wherein:
the absorbance value measured is a first area $A_1$, in units of cm$^{-2}$, under a first FTIR absorbance band at about 240 cm $^{-1}$; and
the calibrating the absorbance value to the nitrogen concentration value is achieved using an equation as follows:

$$N(ppma)=(0.2271/Z)A_1^2+0.0317A_1$$

wherein Z is a calibration adjustment factor calculated as a function of an interstitial oxygen concentration of the sample and said annealing temperature.

41. The method of claim 30 wherein:
the absorbance value measured is a second area $A_2$, in units of cm$^{-2}$, under a second FTIR absorbance band at about 249 cm$^{-1}$; and the calibrating the absorbance value to the nitrogen concentration value is achieved using an equation as follows:

$$N(ppma)=(0.2766/Z)A_2^2+0.032A_2$$

wherein Z is a calibration adjustment factor calculated as a function of an interstital oxygen concentration of the sample and said annealing temperature.

42. The method of claim 30 wherein:
the absorbance value measured is a first area $A_1$, in units of $cm^{-2}$, under a first FTIR absorbance band at about 240 $cm^{-1}$ and a second area $A_2$, in units of $cm^{-2}$, under a second FTIR absorbance band at about 249 $cm^{-1}$; and
the calibrating the absorbance value to the nitrogen concentration value is achieved using an equation as follows:

$$N(ppma)=(0.0618/Z)(A_1+A_2)^2+0.0165\,(A_1+A_2)$$

wherein Z is a calibration adjustment factor calculated as a function of an interstital oxygen concentration of the sample and said annealing temperature.

43. The method of claim 30 comprising normalizing the absorbance value to a standard thickness prior to calibrating the absorbance value to the nitrogen concentration value.

44. A method for detecting a measurement of concentration of nitrogen in a silicon sample by Fourier Transform infrared spectroscopy, the method comprising:
annealing the silicon sample at an annealing temperature $T_a$ for an annealing time $t_a$ to saturate the silicon sample with nitrogen-oxygen complexes, wherein $t_a$ is selected as a function of a detection limit for the nitrogen-oxygen complexes;
performing Fourier Transform infrared spectroscopy to measure an absorbance value related to the concentration of nitrogen-oxygen complexes in the annealed silicon sample; and
calibrating the absorbance value to a nitrogen concentration value.

45. The method of claim 44 wherein in $T_a$ is between about 500° C. and about 750° C.

46. The method of claim 44 wherein $T_a$ is an annealing temperature which results in saturation of the silicon sample with nitrogen-oxygen complexes for an annealing time $t_a$ that is between about 2 minutes and about 290 hours.

47. The method of claim 44 wherein $T_a$ is between about 600° C. to about 650° C. and $t_a$ is between about 0.5 hours to about 4 hours.

48. The method of claim 44 wherein $T_a$ is selected as a function of a detection limit for the nitrogen-oxygen complexes and as a function of annealing time available to saturate the silicon sample with nitrogen-oxygen complexes.

49. The method of claim 44 comprising:
measuring an interstitial oxygen concentration of the silicon;
calculating a calibration adjustment factor as a function of said initial oxygen concentration; and
calibrating the absorbance value to the nitrogen concentration value using said calibration adjustment factor.

50. The method of claim 44 comprising:
measuring an interstitial oxygen concentration of the sample;
calculating a calibration adjustment factor as a function of said initial oxygen concentration and said annealing temperature; and
calibrating the absorbance value to the nitrogen concentration value using said calibration adjustment factor.

51. The method of claim 44 wherein the Fourier Transform infrared spectroscopy is performed while illuminating the silicon sample with white light to eliminate compensation due to donors and acceptors.

52. The method of claim 44 wherein the absorbance value comprises a value selected from among values consisting of a height corresponding to an absorption band at about 240 $cm^{-1}$, an area corresponding to an absorption band at about 240 $cm^{-1}$, and a combination thereof.

53. The method of claim 44 wherein the absorbance value comprises a value selected from among values consisting of a height corresponding to an absorption band at about 249 $cm^{-1}$, an area corresponding to an absorption band at about 249 $cm^{-1}$, and a combination thereof.

54. The method of claim 44 wherein:
the absorbance value measured is selected from values consisting of a first area under a first FTIR absorbance band for nitrogen-oxygen complexes, a second area under a second FTIR absorbance band for nitrogen-oxygen complexes, and a sum of said first area and said second area; and
the calibrating the absorbance value to the nitrogen concentration value is achieved using an equation selected as a function of which said values are selected for said absorbance value.

55. The method of claim 44 wherein:
the absorbance value measured is a first area $A_1$, in units of $cm^{-2}$, under a first FTIR absorbance band at about 240 $cm^{-1}$; and
the calibrating the absorbance value to the nitrogen concentration value is achieved using an equation as follows:

$$N(ppma)=(0.2271/Z)A_1^2+0.0317A_1$$

wherein Z is a calibration adjustment factor calculated as a function of an interstitial oxygen concentration of the sample and said annealing temperature.

56. The method of claim 44 wherein:
the absorbance value measured is a second area $A_2$, in units of $cm^{-2}$, under a second FTIR absorbance band at about 249 $cm^{-1}$; and the calibrating the absorbance value to the nitrogen concentration value is achieved using an equation as follows:

$$N(ppma)=(0.2766/Z)A_2^2+0.032A_2$$

wherein Z is a calibration adjustment factor calculated as a function of an interstital oxygen concentration of the sample and said annealing temperature.

57. The method of claim 44 wherein:
the absorbance value measured is a first area $A_1$, in units of $cm^{-2}$, under a first FTIR absorbance band at about 240 $cm^{-1}$ and a second area $A_2$, in units of $cm^{-2}$, under a second FTIR absorbance band at about 249 $cm^{-1}$; and
the calibrating the absorbance value to the nitrogen concentration value is achieved using an equation as follows:

$$N(ppma)=(0.0618/Z)(A_1+A_2)^2+0.0165(A_1+A_2)$$

wherein Z is a calibration adjustment factor calculated as a function of an interstital oxygen concentration of the sample and said annealing temperature.

58. The method of claim 44 comprising normalizing the absorbance value to a standard thickness prior to calibrating the absorbance value to the nitrogen concentration value.

* * * * *